(12) United States Patent
Bergmann et al.

(10) Patent No.: US 8,691,512 B2
(45) Date of Patent: *Apr. 8, 2014

(54) METHOD FOR THE DETECTION OF SEPSIS BY DETERMINING PEPTIDE PROHORMONE LEVELS

(75) Inventors: Andreas Bergmann, Berlin (DE); Joachim Struck, Berlin (DE); Wolfgang Weglöhner, Berlin (DE)

(73) Assignee: B.R.A.H.M.S. GmbH, Hennigsdorf (DE)

( * ) Notice: Subject to any disclaimer, the term of this patent is extended or adjusted under 35 U.S.C. 154(b) by 193 days.

This patent is subject to a terminal disclaimer.

(21) Appl. No.: 12/756,235

(22) Filed: Apr. 8, 2010

(65) Prior Publication Data

US 2011/0008812 A1    Jan. 13, 2011

Related U.S. Application Data

(62) Division of application No. 12/240,500, filed on Sep. 29, 2008, now Pat. No. 7,723,492, which is a division of application No. 10/808,368, filed on Mar. 25, 2004, now Pat. No. 7,498,139, which is a division of application No. 09/806,437, filed as application No. PCT/EP99/07692 on Oct. 13, 1999, now Pat. No. 6,756,483.

(30) Foreign Application Priority Data

Oct. 15, 1998 (DE) .................................. 198 47 690

(51) Int. Cl.
*G01N 33/53*     (2006.01)
*G01N 33/567*    (2006.01)

(52) U.S. Cl.
USPC ................................................ 435/7.1; 435/4

(58) Field of Classification Search
None
See application file for complete search history.

(56) References Cited

U.S. PATENT DOCUMENTS

| | | | |
|---|---|---|---|
| 5,424,221 | A | 6/1995 | Westermark et al. |
| 5,639,617 | A | 6/1997 | Bohuon |
| 7,361,473 | B2 | 4/2008 | Valkirs et al. |
| 7,498,139 | B2 * | 3/2009 | Bergmann et al. ............. 435/7.1 |

FOREIGN PATENT DOCUMENTS

| | | |
|---|---|---|
| EP | 0 115 459 A2 | 8/1984 |
| WO | WO-94 04927 | 3/1994 |

OTHER PUBLICATIONS

Balci, C. et al., "Usefulness of procalcitonin for diagnosis of sepsis in the intensive care unit," Critical Care, 2003, vol. 7, pp. 85-90.
Bergmann, Lebenslauf—Dr. Andreas Bergmann, 2009.
Bone, R. C. et al., "Definitions for sepsis and organ failure and guidelines for the use of innovation therapies in sepsis. The ACCP/SCOM Consensus Conference Committee. American College of Chest Physicians/ Society of Critical Care Medicine," Chest, 1992, vol. 101, pp. 1644-1655.
Brandt, I. et al., "Dipeptidyl-peptidase IV Converts Intact B-Type Natriuretic Peptide into Its des-SerPro Form," Clinical Chemistry, 2006, vol. 52, No. 1, pp. 82-87.
Brazeau, P. et al., "High biological activity of the synthetic replicates of somatostatin-28 and somatostatin-25," Regulatory Peptides, Jan. 1981, vol. 1, No. 4, pp. 255-264.
Christ-Crain, M. et al., "Mid-regional pro-adrenomedullin as a prognostic marker in sepsis: an observational study," Critical Care, 2005, vol. 9, No. 6, R816-824.
Docherty, K. et al., "Post-Translational Proteolysis in Polypeptide Hormone Biosyntheis," Annual Review of Physiology, Mar. 1982, vol. 44, pp. 625-638.
Duckworth, W. C. et al., "Conversion of biosynthetic human proinsulin to partially cleaved intermediates by collagenase proteinases adsorbed to isolated rat adipocytes," Biochem, J., 1988, vol. 255, pp. 277-284.
Eberlein, G, A. et al., "Patterns of Prohormone Processing," The Journal of Biological Chemistry, Jan. 25, 1992, vol. 267, No. 3, pp. 1517-1521.
Endothelin, www.uniprot.org/uniprot/P05305, May 14, 2009.
Ernst, A. et al., "Detection of stable N-terminal protachykinin A immunoreactivity in human plasma and cerebrospinal fluid," Peptides, Jul. 2008, vol. 29, No. 7, pp. 1201-1206.
Ernst, A. et al., "Proenkephalin A 119-159, a stable proenkephalin a precursor fragments identified in human circulation," Peptides, Jul. 2006, vol. 27, No. 7, pp. 1835-1840.
Even, M. S. et al., "Development of a novel ELISA for human insulin using monoclonal antibodies produced in serum-free cell culture medium," Clinical Biochemistry, Jan. 2007, vol. 40, No. 1-2, pp. 98-103.
Ghillani, P. et al., "Monoclonal antipeptide antibodies as tools to dissect closely related gene products. A model using peptides encoded by the calcitonin gene," Journal of Immunology, 1988, vol. 141, No. 9, pp. 3156-3163.
Goodfriend, T. L. et al., "Angiotensin III: (Des-Aspartic Acid)-Angiotensin II," Suppl. I to Circul. Res. vols. 36 and 37, 1975.
Hadjiakis et al., "Differences between Somatostatin-28 and Somatostatin-14 with Respect to Their Biological Effects in Healthy Humans and Acromegalics," Clin. Physiol. Biochem., 1986, vol. 4, pp. 372-383.

(Continued)

*Primary Examiner* — Prema Mertz
(74) *Attorney, Agent, or Firm* — Millen, White, Zelano & Branigan, PC

(57) ABSTRACT

Uses of recombinant procalcitonin 3-116 in the diagnosis and therapy of septic diseases and the measurement of prohormones other than procalcitonin, and of dipeptidyl peptidase IV, as biomarkers in the diagnosis of sepsis.

25 Claims, 10 Drawing Sheets

(56) References Cited

OTHER PUBLICATIONS

Hallberg, M. et al., "Neuropeptide Conversion to Bioactive Fragments—An Important Pathway in Neuromodulation," Current Protein and Peptide Science, 2003, vol. 4, pp. 31-44.
Hama, N. et al., "Detection of C-type natriuretic peptide in human circulation and marked increase of plasma CNP level in septic shock patients," Biochemical and Biophysical Research Communications, Feb. 14, 1994, vol. 198, No. 3, pp. 1177-1182.
Hemsen, A. et al., "Metabolism of Big endothelin-1 (1-38) and (22-38) in the human circulation in relation to production of endothelin-1 (1-21)," Regulatory Peptides, Feb. 14, 1995, vol. 55, No. 3, pp. 287-297.
Henriksen, J. H. et al., "Increased circulating pro-brain natriuretic peptide (proBNP) and brain natriuretic peptide (BNP) in patients with cirrhosis: relation to cardiovascular dysfunction and severity of disease," Gut, 2003 vol. 52, pp. 1511-1517.
Hirata, Y. et al., "Increased circulating adrenomedullin, a novel vasodilatory peptide, in sepsis," Journal of Clinical Endocrinology & Metabolism, 1996, vol. 81, No. 4, pp. 1449-1453.
Jakubke et al., Peptides, brockhaus abc biochemie, 2. Aufl., 418-421, pp. 456-453, 1975.
Jochberger, S. et al., "Copeptin and Arginine Vasopressin Concentrations in Critically Ill Patients," Journal of Clinical Endocrinology and Metabolism, 2006, vol. 91, No. 11, pp. 4381-4386.
Kimura, S. et al., "Conversion of Big Endothelin-1 to 21-Residue Endothelin-1 is Essential for Expression of Full Vasoconstrictor Activity: Structure-Activity Relationships of Big Endothelin-1," Journal of Cardiovascular Pharmacology, 1989, vol. 13, Suppl. 5, pp. S5-S7.
Köhrle, Gutachten zu Big-Endothelin, 2008.
Krieger et al., Brain Peptides, 80-99, 1983.
Leiting, B. et al., "Catalyric properties and inhibition and of proline-specific dipeptidyl peptidases II, IV, and VII," Biochem. J.,2003, vol. 371, pp. 525-532.
Lubbesmeyer et al., American Journal of Physiology, 1988, (4, Pt. 2) R567-R571.
Lundblad, R. et al., "Endothelin concentrations in experimental sepsis: profiles of big endothelin and endothelin 1-21 lethal peritonitis in rats," Eur. J. Surg., 1995, vol. 161, No. 1, pp. 9-16.
Martin, R. A. et al., "Dipeptidyl peptidase IV (DPP-IV) from pig kidney cleaves analogs of bovine growth hormone-releasing factor (bGRF) modified at position 2 with Ser, Thr or Val. Extended DPP-IV substrate specificity?" Biochimica et Biophysica Acta, Aug. 7, 1993, vol. 1164, No. 3, pp. 252-260.
Mentlein, R. et al., "Dipeptidyl-peptidase IV hydrolyses gastric inhinitory polypeptide, glucagon-like peptide-1(7-36)amide, peptide histidine methionine and is responsible for their degradation in human serum," Eur. J. Biochem, 1993, vol. 214, pp. 829-835.
Millar, R. P. et al., "Somatostatin-28 is an hormonally active peptide secreted into hypophysial portal vessel blood," Brain Research, Feb. 7, 1983, vol. 260, No. 2, pp. 334-337.
Mitaka et al., "Endothelin-1 and atrial natriuretic peptide in septic shock," American Hearth Journal, Aug. 1993, vol. 126, p. 466-468.
Morgenthaler, N. G. et al., "Pro-atrial natriuretic peptide is a prognostic marker in sepsis, similar to the APACHE II score: an observational study," Critical Care, 2004, vol. 9, No. 1, pp. R37-R45.
Müller, B. et al., "Circulating levels of copeptin, a novel biomarker, in lower respiratory tract infections," European Journal of Clinical Investigation, 2007, pp. 145-152.
Nelson, J. B. et al., "Perioperative Plasma Endothelin-1 and Big Endothelin-1 Concentrations in Elderly Patients Undergoing Major Surgical Procedures," Anesth Analg, 1999, vol. 88, pp. 898-903.
Papassotiriou, J. et al., "Immunoluminometric assay for measurement of the C-Terminal Endothelin-1 Precursor Fragments in Human Plasma," Clinical Chemistry, 2006, vol. 52, No. 6, pp. 1144-1151.
Pittet et al., "Elevated plasma endothelin-1 Concentrations are associated with the severity of illness in patients with sepsis," Annals of Surgery, vol. 213, No. 3, Mar. 1991, pp. 261-264.
POMC, www.uniprot.org/uniprot/P01189, May 14, 2009.
Pschyrembel, de Gruyter, 260. Auflage, 1480, 2004.
Rehfeld, J. F. et al., "Naming progastrin-derived peptides," Regulatory Peptides, Aug. 15, 2004, vol. 120, No. 1-3, pp. 177-183.
Reichlin, S., "Somatostatin," The New England Journal of Medicine, 1983, vol. 309, No. 24, pp. 1495-1501.
Schuetz, P. et al., "Circulating Precursor Levels of Endothelin-1 and Adrenomedullin, Two Endothelium-Derived, Counteracting Substances, in Spesis," Endothelium, 2007, vol. 14, pp. 345-351.
Seidah, N. G. et al., "Eukaryotic protein processing: endoproteolysis of precursor proteins," Current Opinion in Biotechnology, Oct. 1997, vol. 8, No. 5, pp. 602-607.
Sequenz Pra-Pro-ET-1, 2009.
Struck, J. et al., "Proteolytic processing pattern of the endothelin-1 precursor in vivo," Peptides, May 2005, vol. 26, No. 12, pp. 2482-2486.
Struck, Lebenslauf—Dr. Joachim Struck, 2009.
Sugiura, M. et al., "Endotoxin stimulates endothelin-release in vivo and in vitro as determined by radioimmunoassay," Biochemical and Biophysical Research Communications, Jun. 30, 1989, vol. 161, No. 3, pp. 1220-1227.
Thefreedictionary.com, prohormone, 2009.
Watson, J. D. et al., "Plasma levels of neuropeptide tyrosine Y (NPY) are increased in human sepsis but are unchanged during canine endotoxin shock despite raised catecholamine concentrations," Journal of Endocrinology, 1988, vol. 116, pp. 421-426.
Yu, S. S. et al., "Biological Activity of Proinsulin and Related Polypeptides in the Fat Tissue," Journal of Biological Chemistry, 1973, vol. 248, No. 11, pp. 3753-3761.
Struyf, S., et al., "Cutting Edge: Enhanced Anti-HIV-1 Activity and Altered Chemotactic Potency of NH2-Terminally Processed Macrophase-Derived Chemokine (MDC) Imply an Additional MDC Receptor," Jrnl. of Immun., Sep. 15, 1998, 161(6): 2672-2675.
Proost, P., et al., "Processing by CD26/dipeptidyl-peptidase IV reduces the chemotactic and anti-HIV-1 activity of stromal-cell-derived factor-1alpha," FEBS Lett., Jul. 31, 1998, 432(1-2): 73-6.
LeMoullec, J.M., et al., "The Complete Sequence of Human Preprocalcitonin," FEBS Lett., Feb. 1984, 167(1): 93-97.
Stader, J.A., et al., "Engineering *Escherchia coli* to Secrete Heterologous Gene Products," Methods in Enzymology, 1990, 185: 166-187.
Neu, H.C., et al., "The Release of Enzymes from *Escherichia coli* by Osmotic Shock and During the Formation of Spheroplasts," J. Biol. Chem., Sep. 1965, 240(9): 3685-3692.
Ghillani, P.P., et al., "Identification and Measurement of Calcitonin Precursors in Serum of Patients with Malignant Diseases," Dec. 1, 1989, 49: 6845-6851.
Pierce Biotech., Inc., Instructions: CarboLink™ Coupling Gel, Jan. 2005, pp. 1-4.
Qi, Y.F., et al., "Effects of Different Peptide Fragments Derived from Proadrenomedullin on Gene Expression of Adrenomedullin Gene," Peptides 23 (2002), pp. 1141-1147.
Richards, A. M., et al., "Plasma N-Terminal Pro-Brain Natiuretic Peptide and Adrenomedullin: New Neurochormonal Predictors of Left Ventricular Function and Prognosis After Myocardial Infarction," Circulation—Journal of the American Heart Association, 1998; 97; 1921-1929—Downloaded from circ.ahajournals.org on Jan. 19, 2010.
Okahara, S., et al., "Serum Pro-Gastrin-Releasing Peptide (PRPGRP) in Subjects With or Without Hericibacter Pyloriinfection", Gastroenterology, U.S. Elsevier, New York, NY, vol. 110, No. 4, Apr. 1996, pp. A217 XP000884904, ISSN: 0016-5085, abstract.
Noriharu, S., et al., "Elevated Progastrin-Releasing Peptide (31-98) Concentrations in Pleural Effusions Due to Small-Cell Lung Carcinoma", Respiration, CH, Karger, Basel, vol. 63, No. 2, Mar. 1, 1996, pp. 106-110, XP000608937, ISSN: 0025-7931; pp. 107, col. 1, paragraphs 2, 4; p. 107, col. 2, paragraph 4, figure 1; p. 109, col. 2, paragraphs 2, 3.
Miyake, Y., et al., "Pro-Gastrin-Releasing Peptide (31-98 is a Specific Tumor Marker in Patients With Small Cell Lung Carcinoma", Cancer Research, vol. 54, Apr. 15, 1994, pp. 2136-2140, XP002132024, p. 2137, col. 1, line 1- line 7, figure 2.
Guo, Y., et al., "Production of Endothelins by the Ventilatory Muscles in Septic Shock", American Journal of Respiratory Cell and Molecu-

(56) References Cited

OTHER PUBLICATIONS lar Biology, US, American Lung Assocation, New York, NY, vol. 1, No. 3, Sep. 1998, pp. 470-476, XP000879419 ISSN: 1044-1549, pp. 472, col. 2, paragraph 3.

McLoughlin, L., et al., "Characterization of Circulating Pro-Opiomelancocortin-Related Peptides in Human Septic Shock", Journal of Endocrinology, GB, Bristol, vol. 119, No. 1, Oct. 1988, pp. 159-165, XP000879345, ISSN: 0022-0795, abstract, pp. 161, col. 1, paragraph 2.

Nylen, E.S., et al., "Pneumonitis-Associated Hyperprocalcitoninemia", American Journal of Medical Sciences, XX, XX, vol. 312, No. 1, Jul. 1996, pp. 12-18, XP000879269, pp. , ISSN: 0002-9629, 15, col. 1, line 2-line 5, p. 15, col. 2, line 5-line 9.

Karzai W., et al., "Procalcitonin—A New Indicator of the Systemic Response to Severe Infections", Infection, DE, MMV Medizin Verlag, Muenchen, vol. 25, No. 6, Nov. 1997, pp. 329-334, XP000879253, ISSN: 0300-8126, pp. 329, col. 2, paragraph 2.

Assicot, M. , et al., "High Serum Procalcitonin Concentrations in Patients With Sepsis and Infections", The Lancet, GB, Lancet Limited, London, vol. 341, No. 8844, Feb. 27, 1993, pp. 515-518, XP000371780, ISSN: 0140-6736, abstract.

Norlander. T., et al., "Effects of Experimental Mycoplasma Pulmonis Infection on Sensory Neuropeptides and Airway Mucosa in the Rat", European Respiratory Journal, vol. 10, 1997, pp. 2334-2342, XP000925422, abstract, p. 2341, col. 1, paragraph 2.

Kullertz, G., "Die Bedeutung Der Aktivitatsbestimmung Des Enzyms Dipeptidyl-Peptidase IV (DP IV) Im Klinischen Laboratorium", Lab Med., vol. 12, 1998, pp. 123-130, XP000933866, pp. 123, col. 1—p. 124, col. 1, paragraph 1, p. 125, col. 1, paragraph 2-paragraph 3, table 4, p. 128, col. 1, paragraph 2, p. 129, col. 1, paragraph 4-paragraph 5.

Qureshi, N. U., et al., "Endogenous Neuropeptide Y Mediates Vasoconstriction During Endotoxic and Hermorragic Shock", Regulatory Peptides. vol. 75-76, Sep. 25, 1998, pp. 215-220, XP000925467—abstract, pp. 215, col. 1-col. 2, line 3, p. 219, col. 1, paragraph 3.

Vanham, G., et al., "Decreased Expression of the Memory Marker CD26 on Both CD4 + CD8 + T Lymphocytes of HIV-Infected Subjects", Journal of Acquired Immune Deficiency Syndromes, vol. 6, No. 7, Jul. 1993, pp. 749-757, XP000925435, p. 751, col. 1, paragraph 6, p. 753, col. 2, paragraph 3, p. 756, col. 1, paragraph 2.

Yaron, A., et al., "Proline-Dependent Structural and Biological Properties of Peptides and Proteins", Critical Reviews in Biochemistry and Molecular Biology, vol. 28, 1993, pp. 31-81, XP000925565, p. 55, col. 1, line 15—col. 2, p. 56, col. 2, paragraph 2—p. 57, col. 1, line 3.

Oravecz, T., et al., "Regulation of the Receptor Specificity and Function of the Chemokine Rantes (Regulated on Activation, Normal T Cell Expressed and Secreted) by Dipeptidyl Peptidase IV (CD26)—Mediated Cleavage", Journal of Experimental Medicine, JP, Tokyo, vol. 186, No. 11, Dec. 1, 1997, pp. 1865-1872, XP002056059, ISSN: 0022-1007, the whole document.

Proost, P., et al., "Amino-Terminal Truncation of Chemokines by CD26/Dipeptidyl-Peptidase IV", Journal of Biological Chemistry, US, American Society of Biological Chemists, Baltimore, MD. vol. 273, No. 13, Mar. 27, 1998, pp. 7222-7227-7227, XP002102982 ISSN: 0021-9258, the whole document.

Wrenger, S., et al., "Amino-Terminal Truncation of Procalcitonin, a Marker for Systemic Bacterial Infections, by Dipeptidyl Peptidase IV (DP IV)", FEBS Letters (Jan. 21, 2000), vol. 466, No. 1, pp. 155-159, XP002143500, the whole document.

Nylen, E.S., et al., "Mortality is Increased by Procalcitonin and Decreased by an Antiserum Reactive to Procalcitonin in Experimental Sepsis", Crit. Care Med., 1998, vol. 26, No. 6, pp. 1001-1006.

Coillie, E.V., et al., "Functional Camparison of Two Human Monocyte Chemotactic Protein-2 Isoforms, Role of the Amino-Terminal Pyroglutamic Acid and Processing by CD26/Dipeptidyl Peptidase IV", Biochemistry 1998, 37, pp. 12672-12680, Published on Web Aug. 18, 1998.

Stieber, P., et al., Pro-Gastrin-Releasing Peptide (PROGRO)—A New Marker in Small-Cell Lung Carcinomas, J. Lab Med. 1997, 21(6), pp. 336-344.

"Grounds of Appeal," in Opposition to EP B1 1 121 600, English translation, Dec. 21, 2009.

Hemsen, A., et al., "Metabolism of Big endothelin-1 (1-38) and (22-38) in the human circulation in relation to production of endothelin-1 (1-21)," Regulatory Peptides, 55 (1995), pp. 287-297.

Hirata, Y., et al., "Receptor binding and vasoconstrictor activity of big endothelin," European Journal of Pharmacology, 176 (1990) pp. 225-228.

Kido, T., et al., "Processing of proendothelin-1 at the C-terminus of big endothelin-1 is essential for proteolysis by endothelin-converting enzyme-1 in vivo," Eur. J. Biochem., 244 (1997), pp. 520-526.

Kimura, S., et al., "Conversion of Big Endothelin-1 to 21-Residue Endothelin-1 Is Essential for Expression of Full Vasoconstrictor Activity: Structure-Activity Relationships of Big Endothelin-1," Journal of Cardiovascular Pharmacology, 13 (Suppl. 5) : S5-S7 (1989).

Krieger, D.T., et al., Biosynthesis and Processing of Neuropeptides, Brain Peptides, 1983, pp. 79-99.

Nelson, J.B., et al., "Perioperative Plasma Endothelin-1 and Big-Endothelin-1 Concentrations in Elderly Patients Undergoing Major Surgical Procedures," Anest Analg, 1999; 88: pp. 898-903.

Neuser, D., et al., "$^{125}$I-Endothelin-1 and $^{125}$I-big endothelin-1 in rat tissues: autoradiographic localization and receptor binding," Histochemistry (1991) 95: 621-628.

Papassotiriou, et al., "Immunoluminometric Assay for Measurement of the C-terminal Endothelin-1 Precursor Fragment in Human Plasma," Clinical Chemistry, 52:6, pp. 1144-1151 (2006).

Pschyrembel, 260.Auflage mit CD-ROM, Cover Page and p. 1480, (2009).

Struck, J., et al., "Proteolytic processing pattern of the endothelin-1 precursor in vivo," Peptides, 26 (2005), pp. 2482-2486.

* cited by examiner

METHOD FOR THE DETECTION OF SEPSIS BY DETERMINING PEPTIDE PROHORMONE LEVELS

This application is a divisional of U.S. patent application Ser. No. 12/240,500, filed Sep. 29, 2008, now U.S. Pat. No. 7,723,492 which is a divisional of U.S. patent application Ser. No. 10/808,368, filed Mar. 25, 2004, now U.S. Pat. No. 7,498,139, which is a divisional of U.S. patent application Ser. No. 09/806,437, filed May 29, 2001, now U.S. Pat. No. 6,756,483, which is a national stage of PCT/EP99/07692, filed Oct. 13, 1999.

The present invention relates to novel diagnostic and therapeutic possibilities which could be derived from novel, experimentally confirmed discoveries in connection with the occurrence of procalcitonin or procalcitonin partial peptides in sepsis and severe sepsis-like systemic infections.

The patents DE 42 27 454 and EP 0 656 121 B1 and U.S. Pat. No. 5,639,617 disclose that the determination of the prohormone procalcitonin and of partial peptides derived therefrom in a serum or plasma of a patient in whom there is a risk of sepsis and in whom symptoms typical of sepsis are found is a valuable diagnostic aid for early detection, i.e. for the detection of infections which may lead to sepsis, and their differentiation from noninfectious etiologies, for the detection of the severity and for the assessment of the success of a treatment of sepsis and sepsis-like systemic infections. Said determination has proved particularly valuable for diagnosis to distinguish symptoms attributable to systemic microbial infections from other symptoms of noninfectious etiology which, owing to their clinical picture, might suggest a sepsis but in reality are not attributable to a systemic microbial infection, for example from symptoms attributable to noninfectious inflammations of individual organs, to postoperative rejection reactions or cancers. Furthermore, systemic inflammations can be distinguished from local ones.

For an overview of the more recent discoveries, reference is made to W. Karzai et al. in Infection, Vol. 25 (1997), 6, pages 329-334 and the further technical literature cited or mentioned therein.

Procalcitonin became known as a prohormone of calcitonin, and its complete amino acid sequence has long been known (FEBS 167 (1984), page 93-97). Procalcitonin is produced under normal conditions in the C cells of the thyroid gland and then specifically cleaved into the hormone calcitonin and the further partial peptides katacalcin and an N-terminal residue comprising 57 amino acids ("aminoprocalcitonin").

Since in the case of sepsis greatly elevated procalcitonin levels are observed even in patients from whom the thyroid gland was completely removed, it was necessary to conclude that the procalcitonin detectable in the blood of sepsis patients is formed outside the thyroid gland, different opinions having been expressed in the technical literature, some of them supported by experimental material, with regard to the organs or cells or the tissues which are critical for procalcitonin production during sepsis.

Regarding the nature of the peptide determined as "procalcitonin" in sepsis, it was in fact made clear from the outset in the above-mentioned patents that the specific peptide need not be completely identical to the known procalcitonin peptide of full length, which is formed in the thyroid glands as a calcitonin precursor. However, the question as to whether the procalcitonin formed in the case of sepsis differs from the procalcitonin formed in the thyroid glands remain unanswered to date. Possible differences were posttranslational modifications of the known procalcitonin, such as glycosylations, phosphorylations or modifications of the primary structure, but also modified, shortened or lengthened amino acid sequences. Since the analytical assay methods used to date did not reveal any differences between the procalcitonin known as the calcitonin precursor and the procalcitonin formed in the case of sepsis, it was provisionally generally assumed that the procalcitonin formed in the case of sepsis is identical to the calcitonin precursor and is thus a peptide having the known procalcitonin sequence of 116 amino acids (procalcitonin 1-116).

As revealed by the determinations in the Applicant's laboratory, explained in more detail in the experimental section of this application, however, the procalcitonin formed in the case of sepsis differs slightly but significantly from the complete procalcitonin 1-116 formed in the thyroid gland. The differences found then led to a number of scientific conclusions which could be implemented in novel diagnostic and therapeutic methods, substances usable therein and scientific approaches which could be pursued.

The starting point for the invention disclosed in the present patent application is the surprising discovery that the procalcitonin detectable in comparatively high concentrations in the serum of patients in the case of sepsis and sepsis-like systemic infection is not the complete procalcitonin 1-116 comprising 116 amino acids but procalcitonin shortened at the amino terminus by a dipeptide but otherwise identical and having an amino acid sequence of only 114 amino acids (procalcitonin 3-116).

The dipeptide missing in comparison with the complete procalcitonin has the structure Ala-Pro. The lack of a dipeptide comprising a proline residue as a second amino acid of the amino terminus of the complete procalcitonin sequence led to the presumption that a specific peptidase might play a role in the production of the procalcitonin 3-116 detectable in the case of sepsis, that is to say the so-called dipeptidyl-(amino)-peptidase IV (DP IV or DAP IV or CD26).

For the determination of a possible role of the dipeptidyl-aminopeptidase IV in association with systemic infection or with sepsis, the inventors have therefore tested experimentally whether a correlation of the physiological DAP IV concentrations with the detection of a sepsis is possible. The results obtained showed such a correlation.

The more exact results obtained furthermore led to the development of a hypothesis that the occurrence of high procalcitonin concentrations in the case of sepsis and systemic infections may not be an isolated phenomenon but that in a similar manner elevated concentrations of other prohormones might also be measurable, so that the determination of such prohormones is a possible alternative to the procalcitonin determination or is suitable for supplementing the procalcitonin determination in individual cases or further confirming it in a diagnostically significant manner.

The discovery that it is not the complete procalcitonin 1-116 which is found in the serum of patients in the case of sepsis but a shortened procalcitonin 3-116 is finally also of potential interest for sepsis therapy. An article by Eric S. Nylen et al., Crit. Care Med. 1998, Vol. 26, No. 6, pages 1001-1006 describes experimental findings which indicate that the procalcitonin occurring in the case of sepsis is not only a diagnostically important marker which is formed, for example, as a metabolic waste product but appears to play an active role as a mediator in an inflammation process caused by infection, by virtue of the fact that procalcitonin can maintain and intensify inflammatory reaction. This role of procalcitonin is at present the subject of controversy, and the test results disclosed do not give a concurring picture.

The above-mentioned discovery that a procalcitonin shortened at the amino terminus by two amino acids occurs in the case of sepsis suggests that the procalcitonin which plays an active role in the case of sepsis and other inflammatory systemic infections is likely to be this shortened procalcitonin 3-116, and that studies carried out with the procalcitonin peptide of full length gave different or contradictory results, inter alia for this reason. It is well known that many physiologically active peptides are converted into their actual active form by cleavage, for example an initial elimination of a short peptide residue. A known example is angiotensin in which peptides having considerably different physiological activities are formed from the inactive angiotensinogen having 14 amino acids by successive elimination first of a tetrapeptide and then of a dipeptide and finally of an individual amino acid. The fact that relatively slight modifications of the N-terminus of the physiologically active peptide play a role in the immunological process and can lead to considerable changes in activity in the corresponding peptides has been confirmed by a number of very recent publications, in which however no reference to septic pathological processes is made (cf. for example J. Immunol. 1998, Sep. 15, 161(6): 2672-5; Biochemistry 1998, Sep. 8, 37(36): 12672-80; FEBS Lett. 1998, Jul. 31, 432 (1-2):73-6; J. Biol. Chem. 1998, Mar. 27; 273 (13):7222-7; J. Exp. Med. 1997, Dec. 1; 186(11): 1865-72).

If it is assumed that procalcitonin 3-116 is actively involved in an inflammatory process and that specific molecular receptors or similar specific binders exist for this shortened procalcitonin, novel therapeutic possibilities are opened up for influencing the course of a sepsis with the use of procalcitonin 3-116 or of agonists and antagonists which interact with the receptors for the procalcitonin 3-116 and can thus influence the physiological reaction triggered by it and hence also an inflammatory process. The use of specific binders of procalcitonin 3-116, e.g. selective antibodies, is also a therapeutic approach which is opened up by the discoveries communicated herein.

Finally, that the dipeptidyl-aminopeptidase IV might play a role in the generation of procalcitonin 3-116 in the case of sepsis and systemic infections led to a further hypothesis, namely that it might also be possible to influence a sepsis or a sepsis-like inflammatory process therapeutically by influencing the activity of the dipeptidyl-aminopeptidase IV by blocking it, for example, by suitable selective binders, antibodies or similar receptor molecules.

It is the object of the present patent application to protect under patent law the novel technical teachings arising from the above novel discoveries and conclusions derived therefrom, to the extent that these are accessible to patent protection taking into account the present state of knowledge.

The attached Patent Claims provisionally summarize such protectable teachings. Further protectable teachings may arise for a person skilled in the art from the complete text of the present application taking into account the experimental conditions and experimental results mentioned in the experimental section and the associated explanations. Rights are expressly reserved with regard to the claiming of such teachings by additional claims.

Selected experimental material which backs up the novel discovery or which demonstrates the correctness of the assumptions derived therefrom is presented below with reference to several diagrams.

EXPERIMENTAL SECTION

Figure 1:
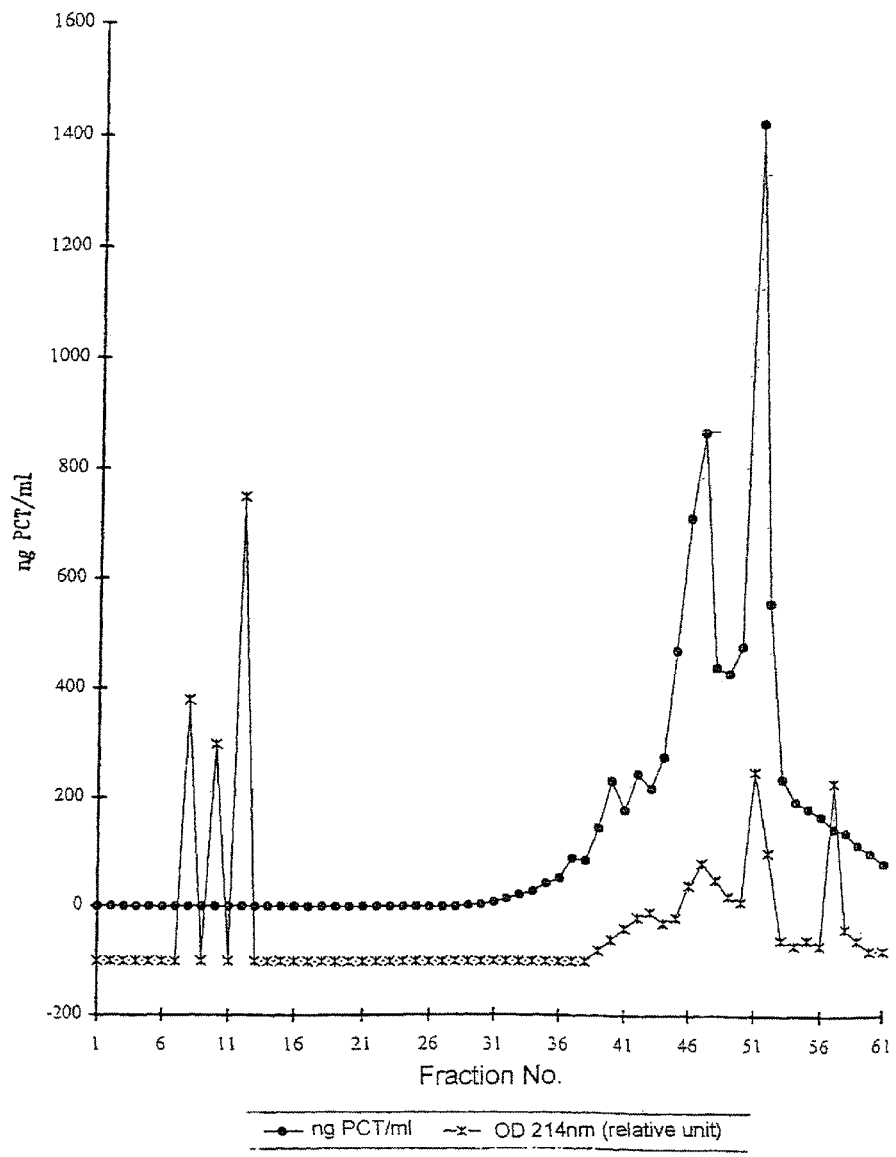
FIG. 1 shows the results of a procalcitonin isolation and purification by HPLC from a pooled serum of collected sera from various patients with severe sepsis.

A. Isolation and Characterization of the Endogenous Procalcitonin Peptide from Sera of Septic Patients By mixing serum samples from different patients suffering from severe sepsis, a mixed serum having a total volume of 68 ml was prepared. The procalcitonin concentration in the pooled serum obtained was determined with the aid of a commercial procalcitonin assay (LUMItest PCT, B.R.A.H.M.S. Diagnostica) as 280 ng/ml (total amount 19 µg). The pooled serum was mixed with an identical volume of a buffer (68 ml; 10 mM EDTA, 1 mg/ml mouse-IgG, 2 mg/ml sheep-IgG, 2 mg/ml bovine IgG, 0.1 mmol leupeptin, 50 µM Amastatin in PBS) and the procalcitonin contained in the sample was isolated and purified by affinity chromatography.

For this purpose, the total pooled sample was pumped at a flow rate of 0.5 ml/min four times in succession over an affinity column (0.5×1 cm, anti-calcitonin antibodies, bound to Carbolink from Pierce, procalcitonin binding capacity about 20 µg). The column was then washed with 30 ml of PBS, and the bound peptide was eluted with the aid of 50 mM acetic acid (pH about 2.0). The column outflow was monitored continuously for absorption at 280 nm, and the protein fraction eluted by the acetic acid was collected (final volume 2.0 ml).

The material collected in this manner was purified by reversed-phase HPLC over an rpC$_{18}$ column µ Bondapak 0.4×30 mm (from Waters). The flow rate was 1 ml/min, and the mobile phase and elution conditions are shown in Table 1 below.

TABLE 1

Elution Conditions for rp-HPLC of Procalcitonin

| | | | |
|---|---|---|---|
| Mobile phase A: | 5% acetonitrile<br>20 mM NH$_4$ acetate | | |
| Mobile phase B: | 90% acetonitrile<br>20 mM NH$_4$ acetate | | |
| Gradient: | 0.0 min | 100% A | 0% B |

TABLE 1-continued

Elution Conditions for rp-HPLC of Procalcitonin

| | | |
|---|---|---|
| 2.5 min | 100% A | 0% B |
| 5.0 min | 89% A | 11% B |
| 55.0 min | 56% A | 44% B |
| 60.0 min | 0% A | 100% B |

The column outflow was measured continuously for its absorption at 214 nm and collected in fractions of 0.25 ml. With the aid of a commercial procalcitonin assay (LUMItest PCT, B.R.A.H.M.S Diagnostica) those fractions in which a PCT immunoreactivity was detectable were determined. It was found that the main immunoreactivity was eluted in the 51st fraction as a sharp band. In addition, protein fractions having a heterogeneous composition and lower PCT immunoreactivities were obtained in fractions 39 to 49.

FIG. 1 shows the PCT immunoreactivity (expressed as ng PCT/ml) determined for the individual collected fractions of the rp HPLC chromatography, superposed with a curve which shows the optical density (OD) of the eluted fractions.

All fractions which had a positive procalcitonin immunoreactivity were dried with nitrogen by gassing. Thereafter, the samples were analyzed by mass spectrometry and subjected to an N-terminal sequencing.

Figure 2:
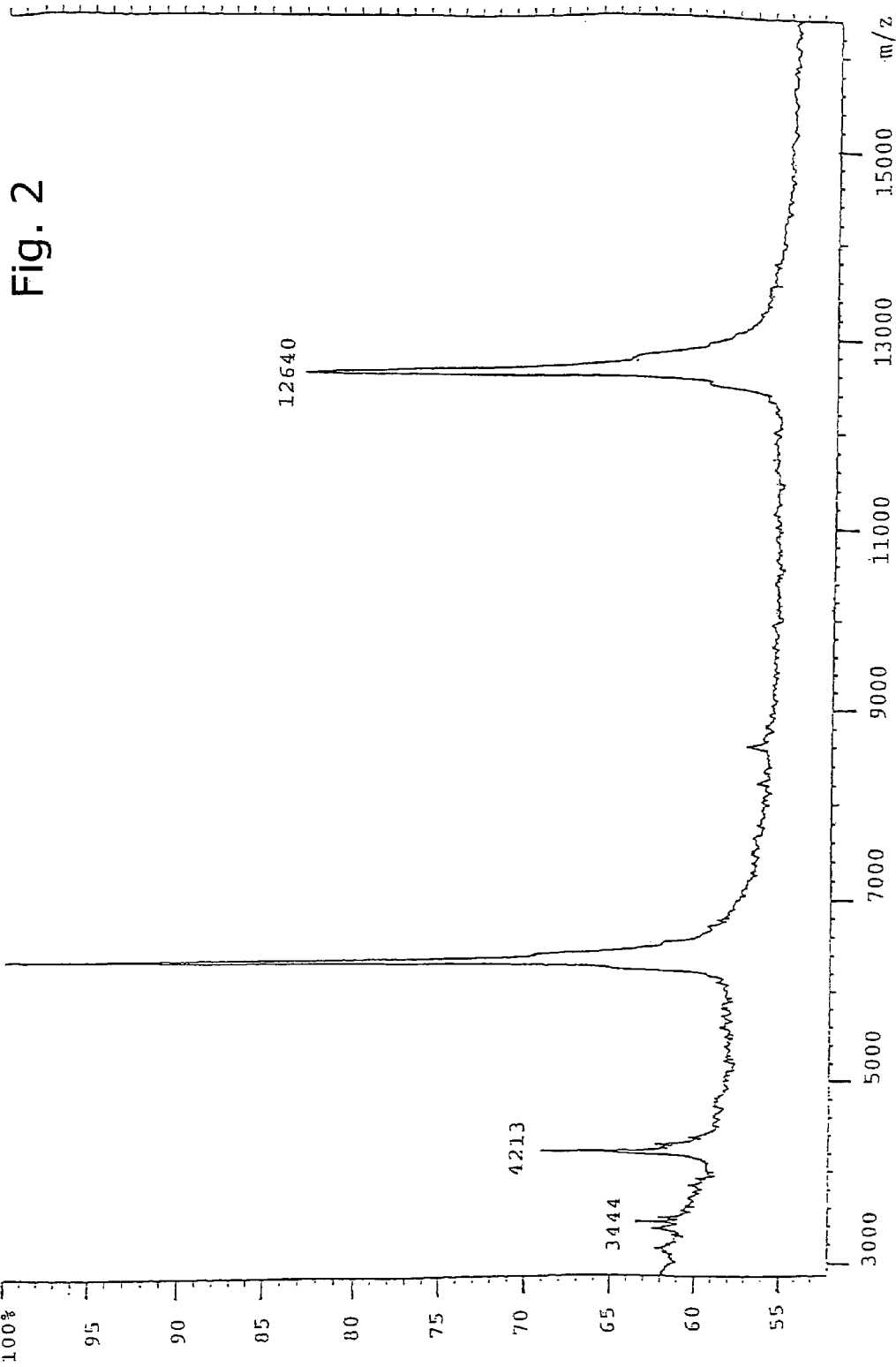
FIG. 2 shows the results of a mass, spectroscopic analysis of those fractions of the pooled serum from FIG. 1 which have a high procalcitonin immunoreactivity.

In the mass spectrometric analysis (MALDI-TOF method), the profile shown in FIG. 2 was obtained for fractions 50-52, from which profile a molar mass of 12640±15 resulted. All other fractions (36-49, 53-59) investigated by mass spectrometry showed heterogeneous mass distributions with molar masses <12640. Their individual mass gave an intensity of <2% in comparison with the intensity of the mass of the fractions 50-52. It was thus demonstrated that the procalcitonin immunoreactivity in sera of patients suffering from sepsis is associated with a mass of 12640±15. None of the fractions obtained had a higher mass.

The peptides contained in fractions 36-59 were subjected to an N-terminal sequencing. Here too, the content of fractions 36-49 and 53-59 proved to be heterogeneous, i.e. a multiplicity of N-termini was determined.

For the fractions 50-52, in which the predominant procalcitonin immunoreactivity was to be found, it emerged that the peptides contained therein clearly have the following N-terminus (15 amino acids):

Phe Arg Ser Ala Leu Glu Ser Ser Pro Ala Asp

Pro Ala Thr Leu

The peptide from fractions 50-52 was then digested by means of protease Glu-C or trypsin, and the resulting fragments were recovered in a manner known per se by means of SMART-HPLC and then investigated by mass spectrometry and sequence analysis.

A sequence which corresponded completely with the sequence of the amino acids 3-116 of the known procalcitonin 1-116 was obtained. The theoretical mass of the sequence was 12627, which is in agreement with the mass of 12640±15 determined by mass spectrometry.

Consequently, it was demonstrated that a procalcitonin peptide which comprises 114 amino acids and is to be designated as procalcitonin 3-116 circulates in the blood of patients suffering from sepsis. The peptide is not changed by posttranslational modifications, such as phosphorylations or glycosylations.

The procalcitonin 3-116 has not yet been discussed to date in the scientific literature as a possible endogenous procalcitonin partial peptide, and there has therefore also been no reason to date for a person skilled in the art specifically to prepare this peptide and to investigate it with regard to its properties. However, the above findings have now provided a reason for the specific preparation of said procalcitonin 3-116 by genetic engineering techniques. Its preparation is described below.

B. Cloning, Expression and Purification of Recombinant Procalcitonin 3-116

1. Cloning

The DNA fragments coding for procalcitonin 3-116 (abbreviated below to PCT 114) were isolated from a human thyroid cDNA pool using PCR amplification with the aid of suitable oligonucleotide primer. The desired fragment was cloned by means of conventional methods (Ausubel F M, Brent R, Kingston R E, Moore D D, Seidman J G, Smith J A and Struhl K (1991), Current Protocols in Molecular Biology, John Wiley & Sons, New York), and the correct nucleotide sequence was verified by DNA sequencing and comparison with the known DNA sequence coding for procalcitonin.

For the expression of the cDNA coding for PCT 114, a vector was used which contains, in addition to a T7 promoter, a region which codes for the signal peptide of the so-called pelB protein. This pelB signal peptide ensures that a fusion protein formed after cloning and expression is transported through the cytoplasmic membrane of the host cells used for the expression into the periplasmic space. During this transport process, the N-terminal signal peptide is simultaneously separated by a signal peptidase located on the membrane (Stader J A and Silhavy T J (1990), Engineering *Escherichia coli* to secrete heterologous gene products, Methods Enzymol. 185, 166-187). This procedure guarantees that the expression product found has exactly the desired sequence. In this procedure, the N-terminal methionine required in other expression methods is absent.

After the cloning of the cDNA for PCT 114 into a vector of said type and transformation of *E. coli* with this vector, procalcitonin 3-116 was expressed. The periplasmic fraction with the expressed procalcitonin 3-116 was isolated in a manner known per se (Neu H C and Heppel L A (1965), The release of enzymes from *Escherichia coli* by osmotic shock and during the formation of spheroblasts, J. Biol. Chem. 240, 3685-3692). After centrifuging (100,000 g, 30 min, 4° C.) and filtration of the liquid supernatant (0.2 µm) the filtrate obtained was separated by anion exchange chromatography. The fractions with procalcitonin immunoreactivity were combined and were purified by reversed-phase HPLC, as described in connection with the isolation of PCT 3-116 from septic sera.

All fractions with procalcitonin immunoreactivity were combined and lyophilized. As shown by checking the material by means of SDS-PAGE, the material thus obtained was at least 95% pure.

The identity of the expressed and purified peptide as procalcitonin 3-116 was confirmed by mass spectrometry and sequence analysis.

The recombinant procalcitonin 3-116 obtained is a novel recombinant peptide and can be used in this form for the preparation of immune reagents and investigated with respect to suitability as a therapeutic or with respect to its ability, in the context of the above-mentioned publication (Eric S. Nylen, loc. cit.), to have prophylactic and therapeutic activity.

For the preparation of calibrators for PCT assays, the method described above for the preparation of procalcitonin 3-116 by genetic engineering was used in essentially identical form also for the preparation of the complete procalcitonin 1-116 and of procalcitonin 2-116.

C. Determination of the Dipeptidyl-Aminopeptidase IV (DAP IV) Activity in Normal Human Sera and Sera from Patients with Severe Sepsis 20 serum samples each from healthy normal persons and from patients suffering from sepsis were investigated with respect to their dipeptidyl-aminopeptidase IV-specific enzyme activity. The DAP IV enzyme activity was measured fluorometrically in a manner known per se using Lys-Pro-4-methoxy-beta-naphthylamide. For this purpose, in each case 2 µA of the serum to be tested with 3 ml of substrate (50 µg/ml Lys-Pro-4-methoxy-beta-naphthylamide, 50 mM Tris/HCl, pH 7.5) and the resulting fluorescence was measured continuously at an emission wavelength of 410 nm with excitation with light having a wavelength of 340 nm. The fluorescence signal was calibrated by means of a 4-methoxynaphthylamine solution. The enzyme activity determined in this manner is stated in nmol/min.

Figure 3:
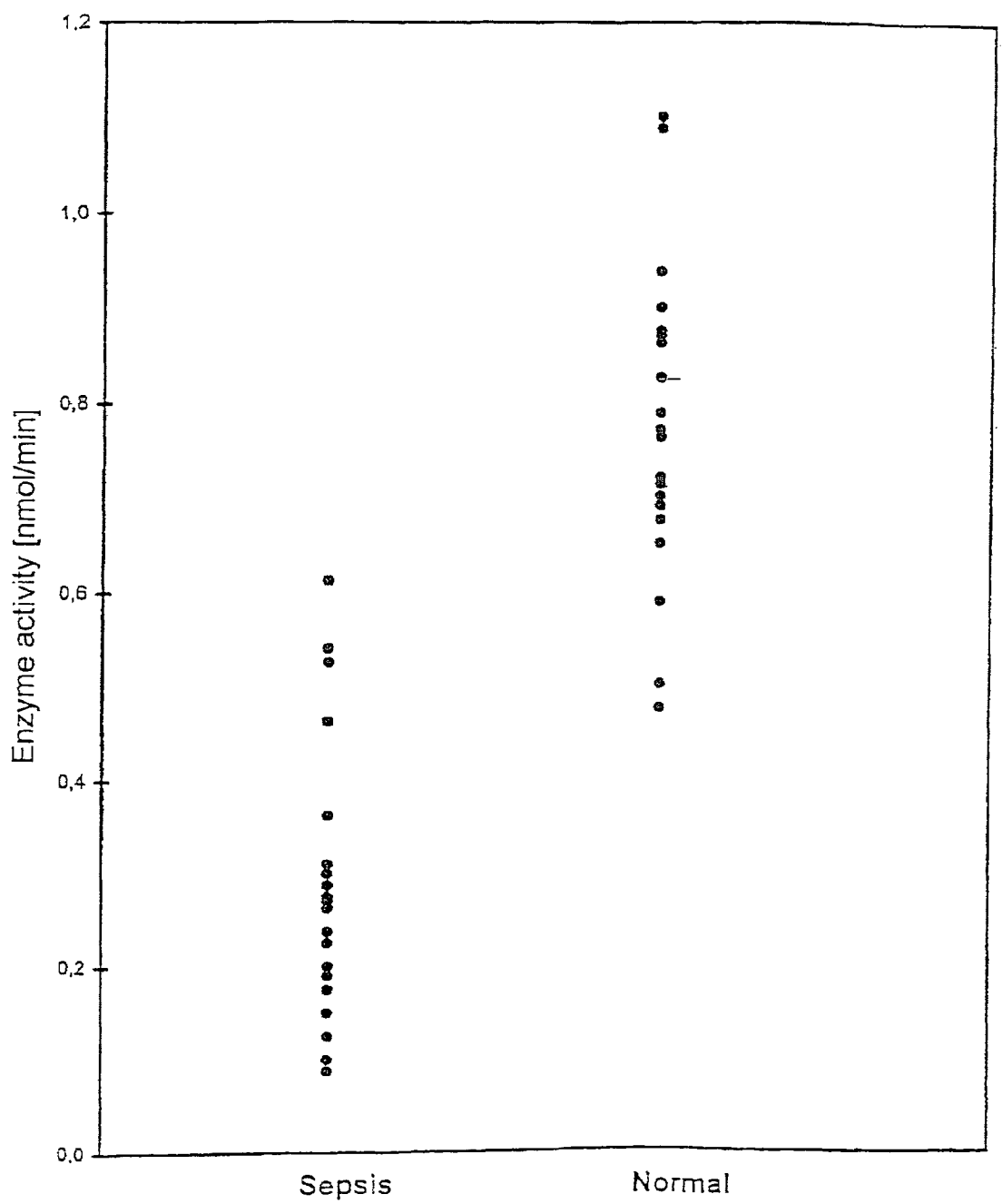
FIG. 3 shows the results of the determination of the enzyme activity of dipeptidyl-aminopeptidase IV in septic sera and normal sera.

The results obtained are shown in FIG. 3.

It is clear that the DAP IV enzyme activity in the sepsis sera is substantially lower than that in the sera of healthy normal persons (blood donor sera). Thus, the determination of the DAP IV enzyme activity in plasma or serum can also be used for detecting sepsis in patients sera.

The substantially reduced plasma concentration of DAP IV in the case of sepsis may be regarded on the one hand as evidence that DAP IV is involved in a sepsis process. On the other hand, the results indicate that it cannot be the concentration of DAP IV in the plasma that is responsible for the formation of procalcitonin 3-116. Rather, the results obtained suggest the conclusion that procalcitonin 3-116 is formed by tissue- or cell-bound DAP IV, possibly intracellularly, and is liberated from procalcitonin-producing or procalcitonin-storing cells.

The information contained in the literature to the effect that DAP IV is expressed from activated T-cells (cf. Hegen and Oravecz, Protein Reviews on the WEB; Fleischer, loc. cit.) indicates a close relationship between the expression of DAP IV and the activity state of the immune system, which, in the case of a septic systemic infection, is under extreme stress and therefore exhibits typical reactions which manifest themselves, inter alia, in greatly increased procalcitonin 3-116 formation.

Apart from the possibilities arising out of the above findings, for determining DAP IV in the course of the sepsis diagnosis, the above results may also indicate that the processes taking place in a cascade-like manner during a sepsis can be influenced therapeutically by DAP IV inhibitors, so that it might be possible to prevent or to reduce the liberation of procalcitonin 3-116 and other hormones or converted prohormones under sepsis, enabling pathological consequences for this prohormone liberation to be reduced or avoided.

D. Determination of the Concentrations of Prohormones Other than Procalcitonin in the Case of Sepsis The fact that it is not the complete prohormone procalcitonin which is released in the case of sepsis, but a modified prohormone shortened by an Xaa-Pro dipeptide, led to the hypothesis that not only is procalcitonin 3-116 liberated in the case of sepsis but procalcitonin 3-116 is perhaps only one representative of a whole group of prohormones or similar peptides, for example those having immunomodulatory properties, which are liberated to a high degree and possibly in converted form in the case of sepsis.

Checking of known prohormones and of the amino acid sequences stated in the literature for these prohormones showed that in actual fact most known prohormones have at the amino terminus a dipeptide which can be defined as Xaa-Pro and which can therefore be eliminated in a sense similar to that observed in the case of procalcitonin. Specifically, dipeptides of said type are present at the amino terminus of a very large number of prohormones or immunomodulators. The following list of literature data in the form of a table gives an overview of some selected prohormones or immunomodulators, the dipeptide to be found in these at the amino terminus and their total number of amino acids.

The prohormones shown in Table 2 are examples of prohormones whose concentrations may be elevated in the case of sepsis, although the list is not to be regarded as exhaustive. In the case of the immunomodulators, elimination of a dipeptide is likely to influence the activity.

TABLE 2

| Prohormone/Immunomodulator | Dipeptide at the N-terminus | Total Number of All Amino Acids |
|---|---|---|
| Pro-Endothelin-1 (pro-END) | Ala Pro | 195 |
| Pro-Brain-natriuretic peptide (pro-BNP) | His Pro | 108 |
| Pro-Atrial-natriuretic peptide (pro-ANP; also pro-atrionatriuretic factor, pro-ANF) | Asn Pro | 128 |
| Pro-Leptin | Val Pro | 146 |
| Pro-Neuropeptide Y | Tyr Pro | 69 |
| Pro-Somatostatin | Ala Pro | 92 |
| Pro-Neuropeptide YY | Thr Pro | 69 |
| Interleukin 6 | Val Pro | 183 |
| Interleukin 10 | Ser Pro | 160 |
| Pro-Gastrin-releasing peptide (pro-GRP) | Val Pro | 115 |
| Pro-Opiomelanocortin | Trp Cys | 241 |
| Pro-Adrenomedullin (pro-ADM) | Ala Arg | 164 |
| Procalcitonin (PCT) | Ala Pro | 116 |

The experimental findings to date actually indicate that, in the case of a systemic infection, such as sepsis, in general prohormones and peptide immunomodulators, such as interleukins, are possibly liberated with modification by elimination of dipeptides at the amino terminus and that these possibly initiate further subsequent steps in the cascade of an immune response by interaction with associated specific receptors or other binders.

Parallel with a procalcitonin determination in normal sera and sera from patients suffering from sepsis, the determination of further prohormones, which had been chosen fairly randomly, was also carried out. These were (i) pro-gastrinreleasing peptide (proGRP), (ii) pro-atrial-natriuretic peptide (pro-ANP or pro-ANF), (iii) pro-adrenomedullin (pro-ADM), (iv) pro-endothelin (pro-END) and (v) pro-brain-natriuretic peptide (pro-BNP).

D.1. Determination of proGRP In Sera from Patients Suffering from Sepsis and from Normal Persons An assay is commercially available for the determination of proGRP. In a recent publication, proGRP is described as a tumour marker in small-cell bronchial carcinoma (Petra Stieber et al., J. Lab. Med. 1997, 21(6):336-344). The assay for the determination of proGRP is commercially available from the Tonen Corporation under the name ProGRP ELISA KIT™.

Figure 4A:
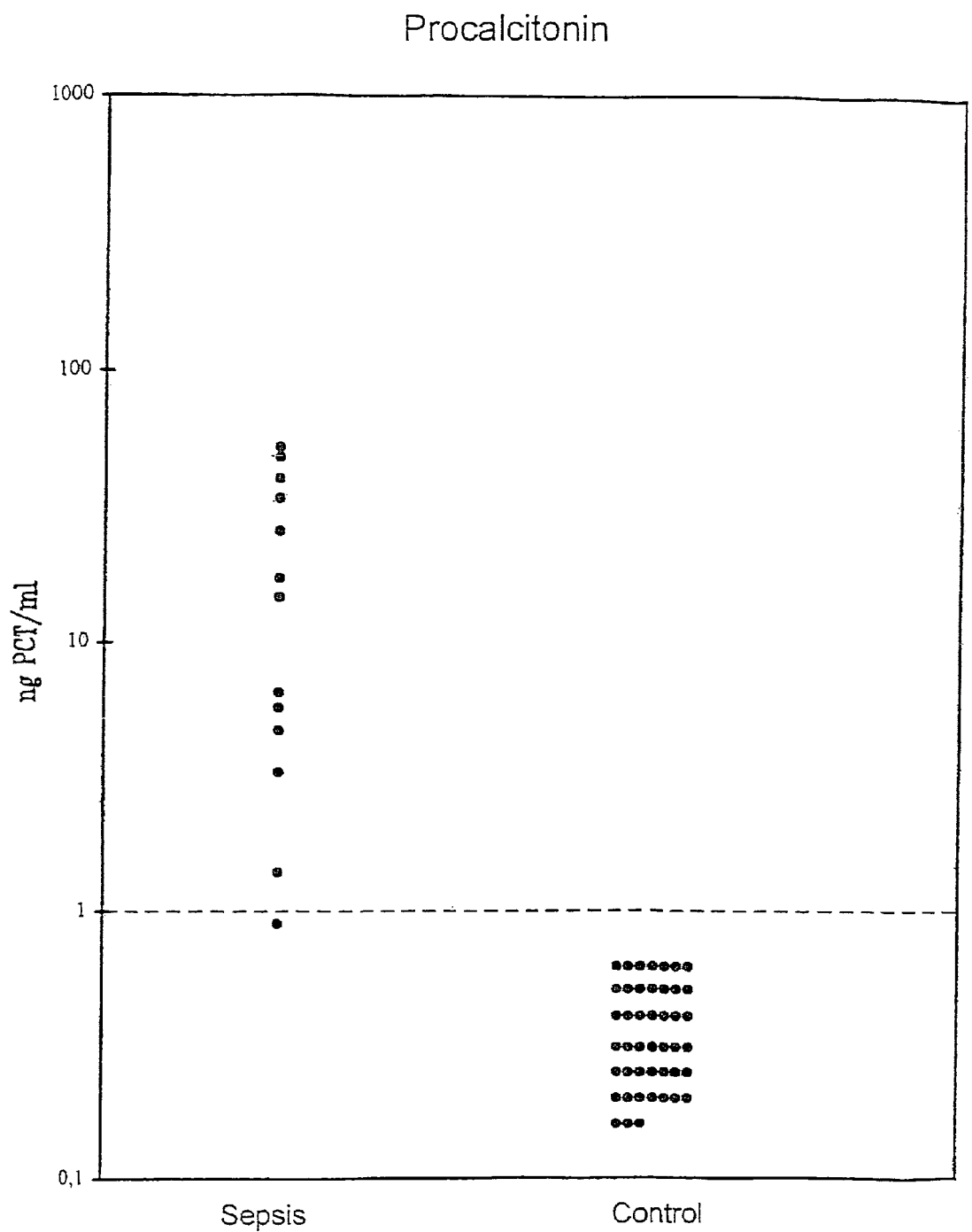
FIG. 4 shows the results of the determination of procalcitonin in septic sera and normal sera in comparison with results of the determination of a further prohormone, namely pro-gastrin-releasing peptide (proGRP), in the same sera.
Figure 4B:
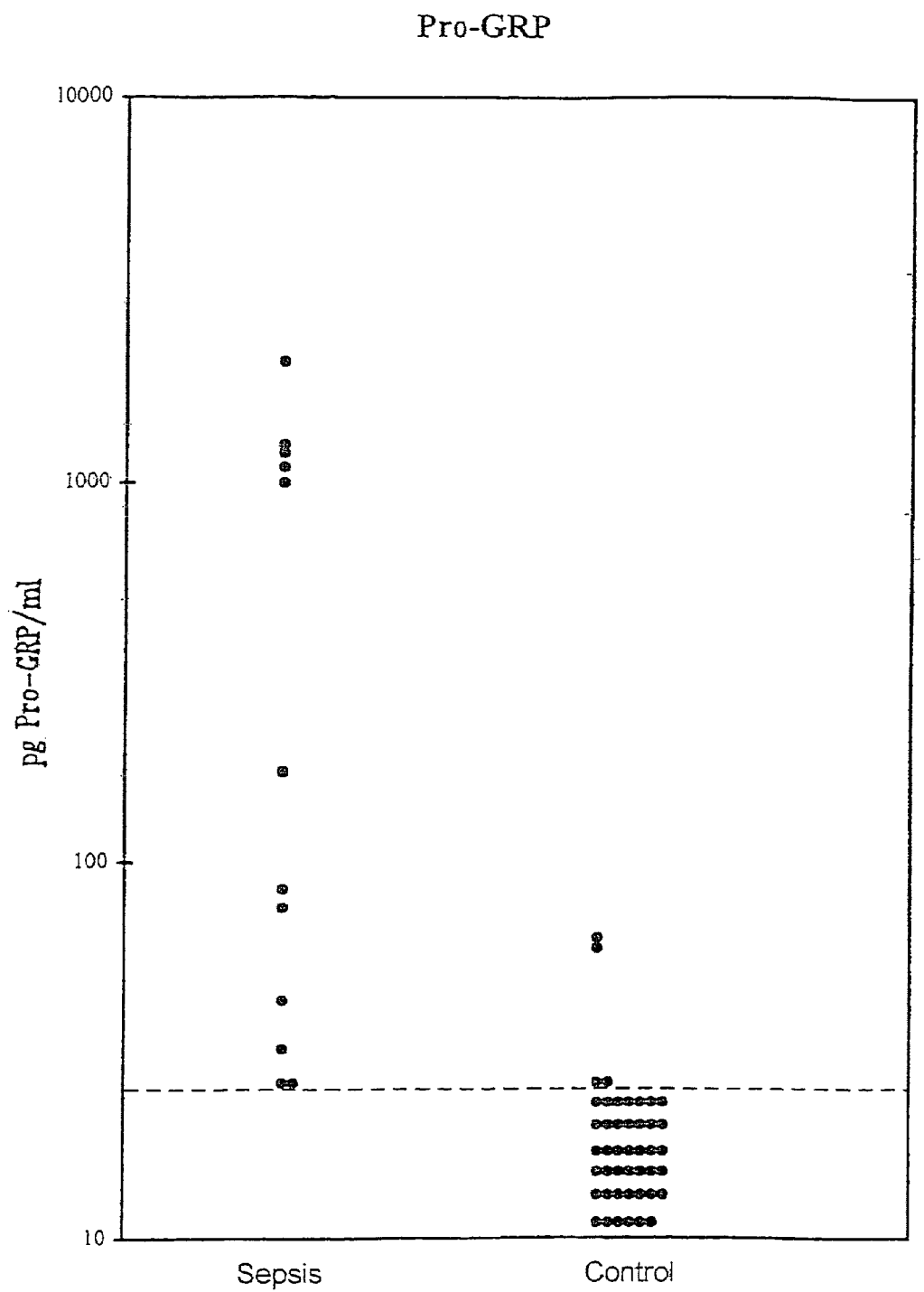
Figure 5:
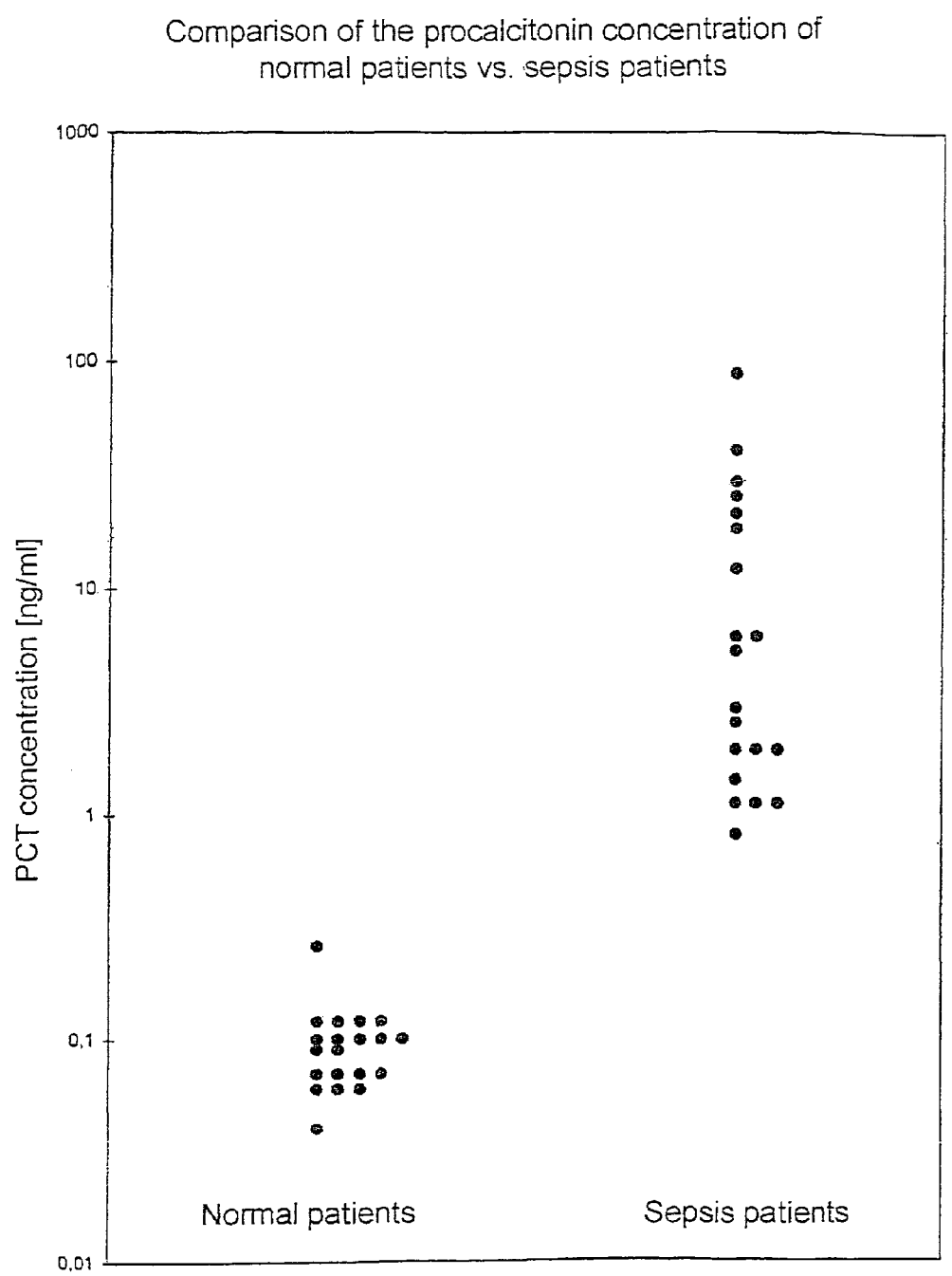
FIG. 5 shows the results of the determination of procalcitonin in sera of a group of 20 normal persons and, on the other hand, 20 patients suffering from sepsis.
Figure 6:
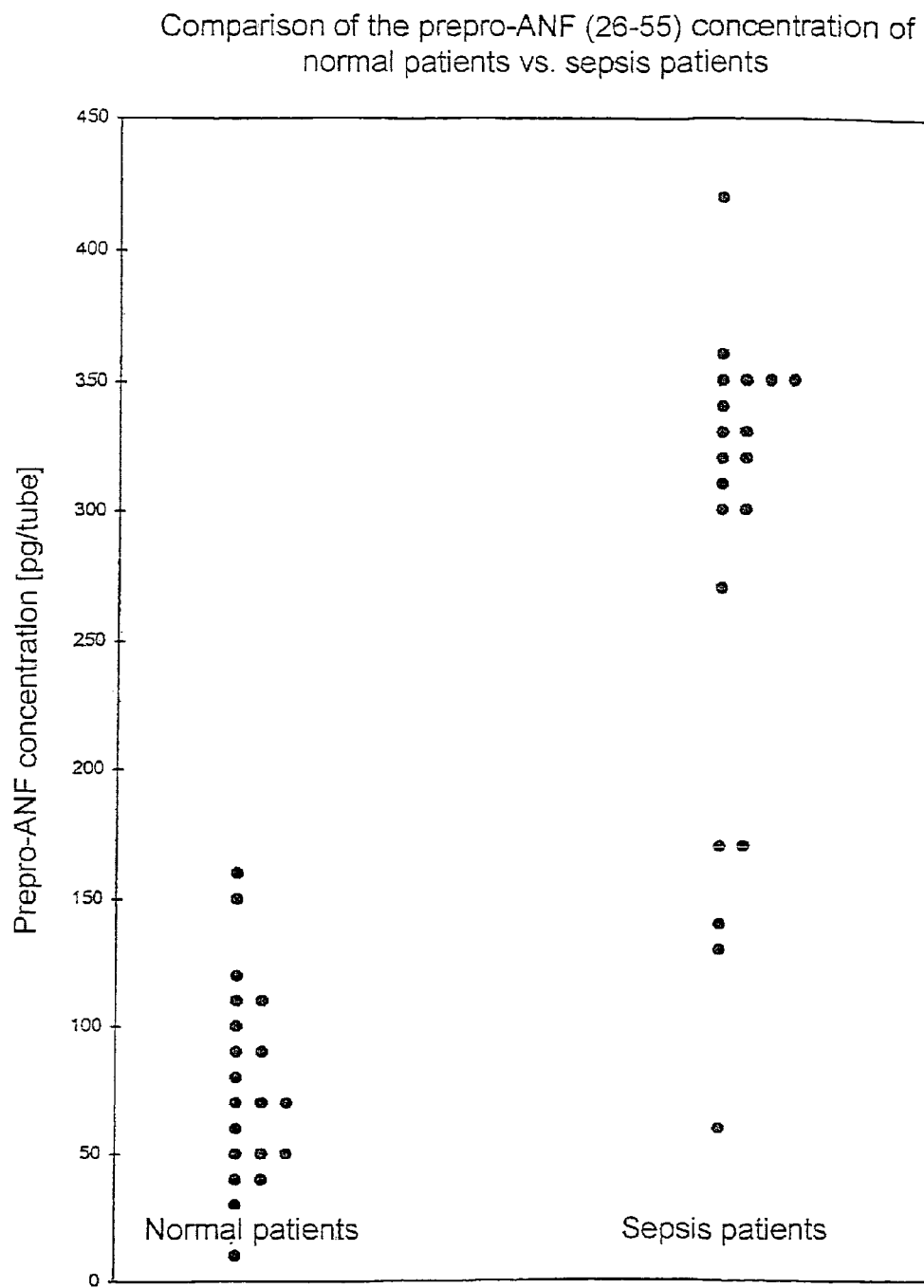
FIG. 6 shows the results of the determination of pro-ANF (in pg/tube) in the same groups of normal persons and patients suffering from sepsis as in FIG. 5.
Figure 7:
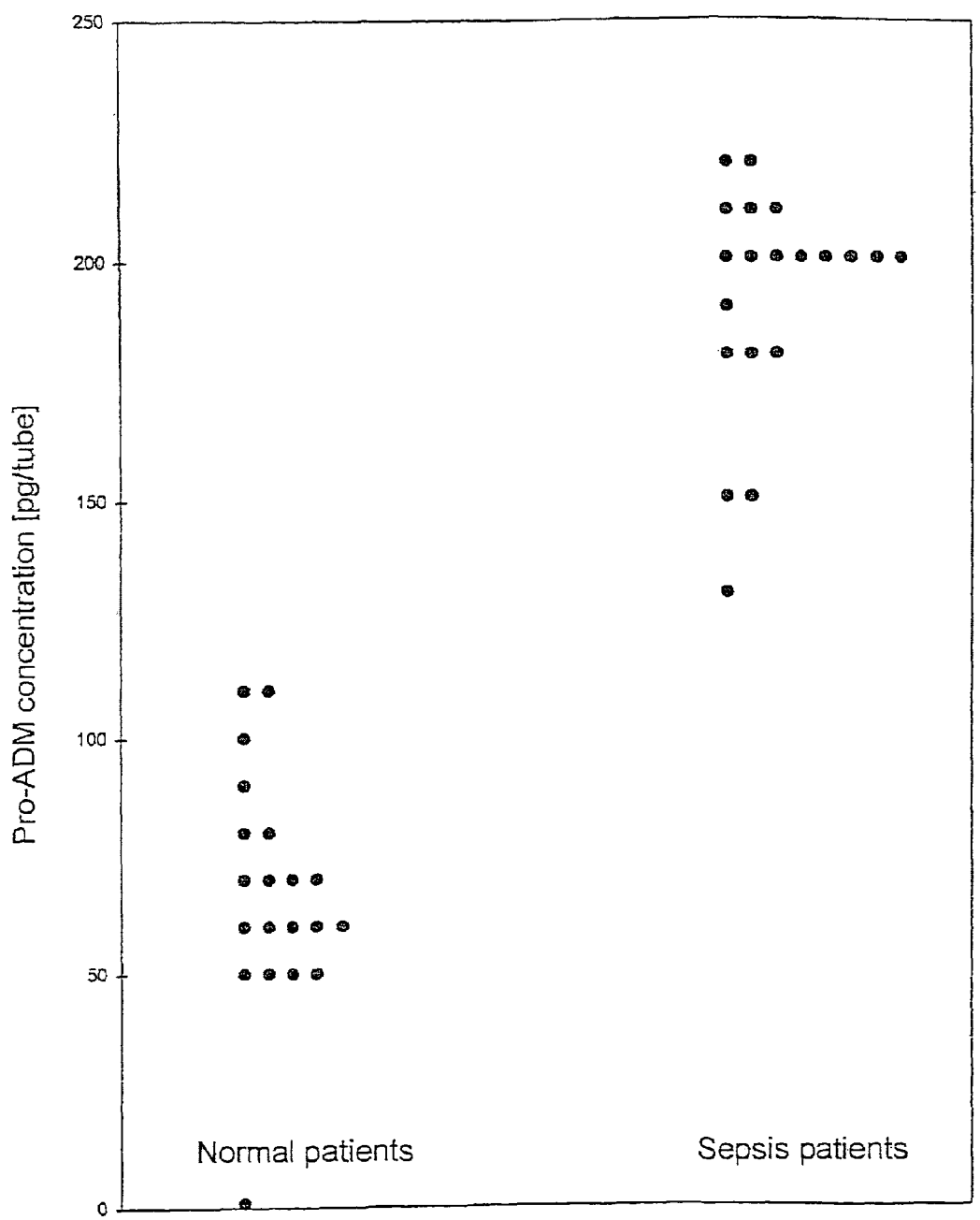
FIG. 7 shows the results of the determination of Pro-ADM (in pg/tube) in the same groups of normal persons and patients suffering from sepsis as in FIG. 5.
Figure 8:
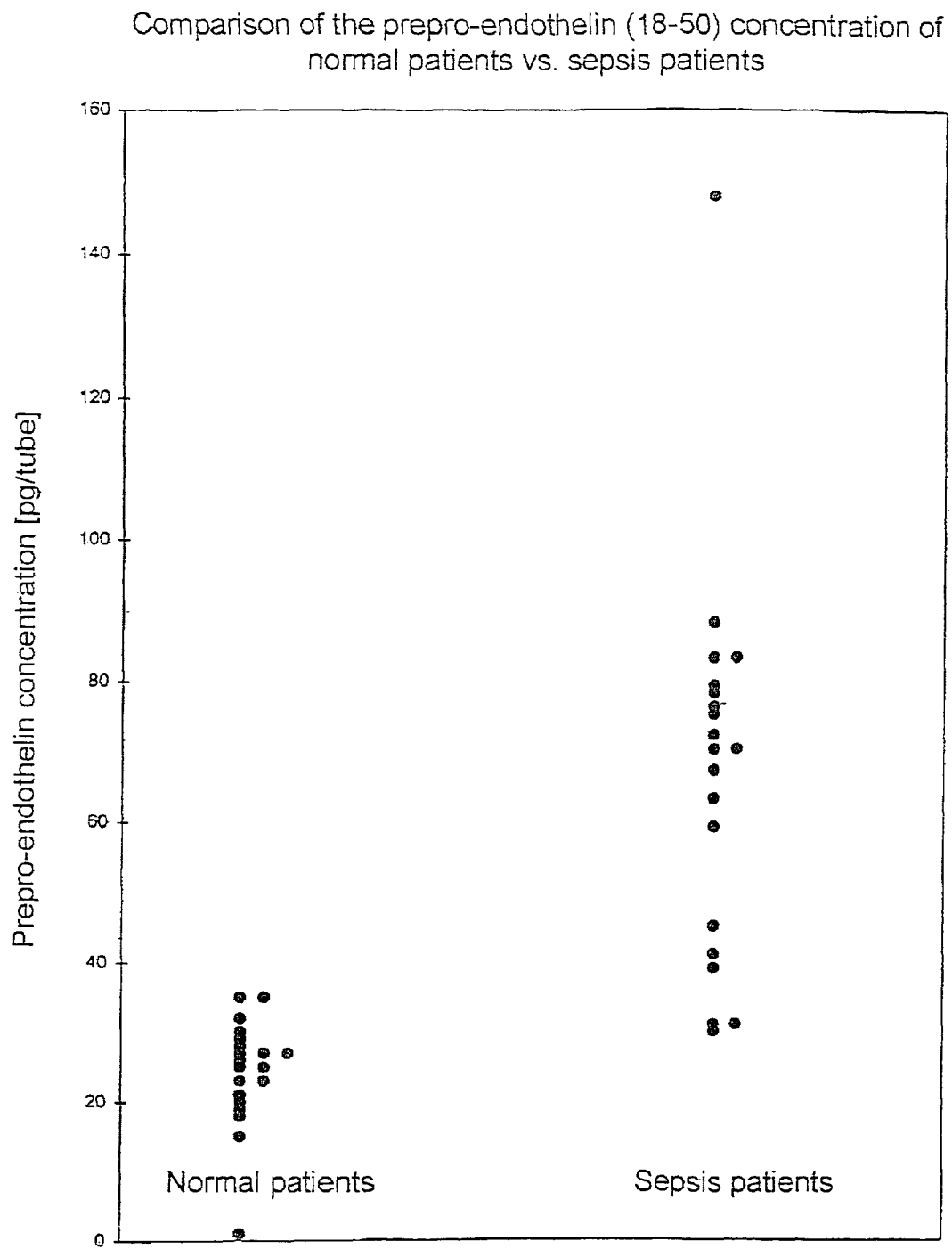
FIG. 8 shows the results of the determination of Pro-END (in pg/tube) in the same groups of normal persons and patients suffering from sepsis as in FIG. 5.
Figure 9:
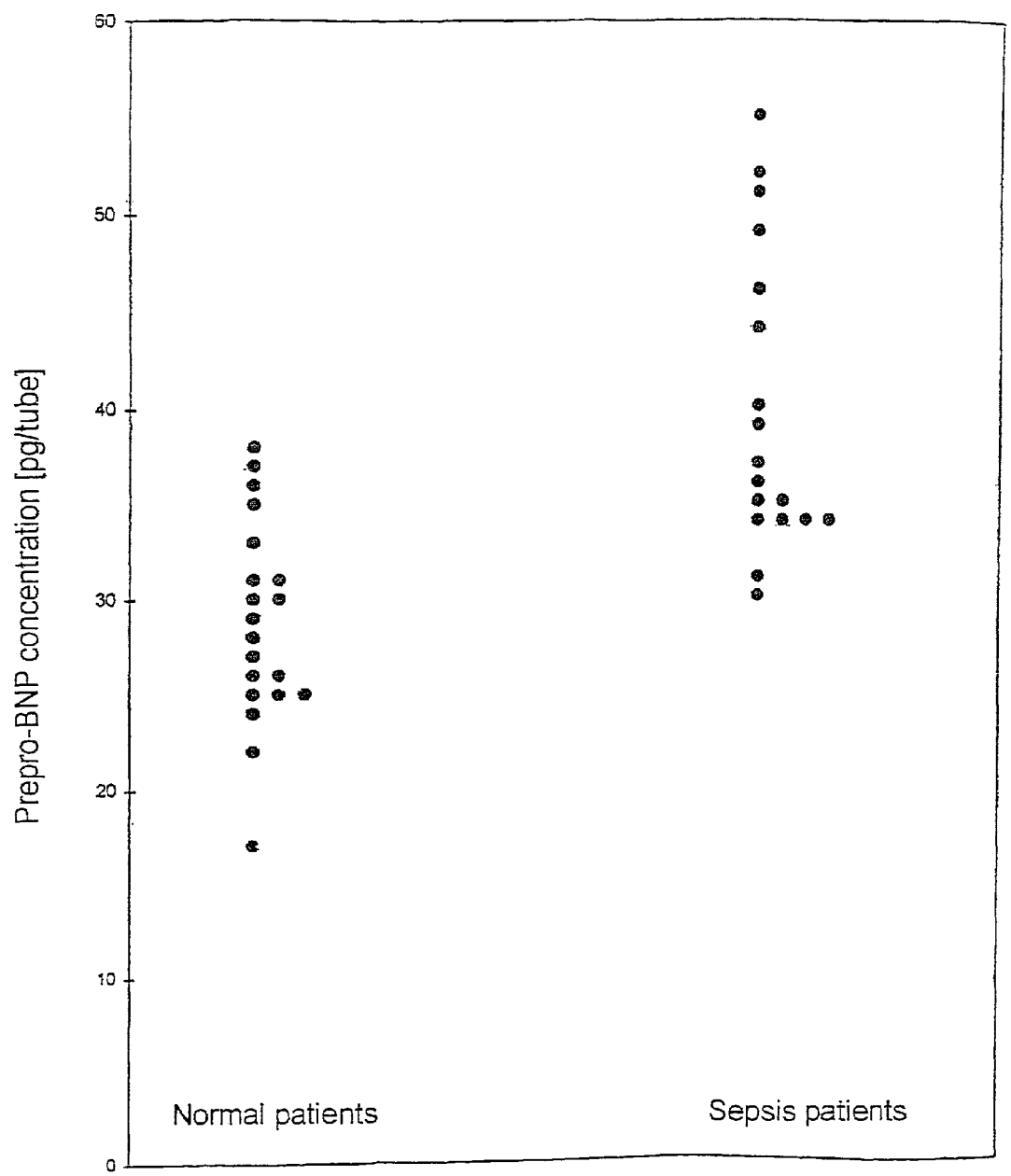
FIG. 9 shows the results of the determination of Pro-BNP (in pg/tube) in the same groups of normal persons and patients suffering from sepsis as in FIG. 5.

Using this kit and following the procedure prescribed in the information for use of the commercial kit, the measured results shown in FIG. 4 were obtained.

A comparison of the values obtained for procalcitonin on the one hand and proGRP on the other hand shows that the distinction between normal sera and sepsis sera is clearer in the case of procalcitonin but that the proGRP concentrations are elevated in a manner substantially similar to those of procalcitonin.

D.2. Determination of pro-ANF, pro-ADM, pro-END and pro-BNP in Sera from Patients Suffering from Sepsis and from Normal Persons For the determination of the (pre)prohormones pro-ANF, pro-ADM, pro-END and pro-BNP, assays are commercially available in kit form from DRG (DRG Instruments GmbH, D-35018 Marburg, Germany) and were used for the following measurements in accordance with the manufacturer's instructions.

Specifically, the following were used:

For the determination of pro-ANF, the Prepro-ANF 26-55 (human) RIA kit; for the determination of pro-ADM, the Pro-Adrenomedullin 45-92 (human) RIA kit; for the determination of pro-END, the Prepro-Endothelin 18-50 (human) RIA kit; and for the determination of Pro-BNP, the Prepro-BNP 22-46 (human) RIA kit from the above-mentioned company DRG.

In the sera of a group of 20 normal persons A-T and of 20 patients suffering from sepsis, the above-mentioned prohormones and, parallel to these, procalcitonin were determined. The results are summarized in Table 3 below. The data in Table 3 are also shown graphically in FIGS. 5 to 9.

The results shown show a more or less clear increase in the values for all measured prohormones in the case of patients suffering from sepsis compared with normal persons, although the distinction between normal persons and patients suffering from sepsis is most pronounced in the determination of procalcitonin.

The supplementary literature search furthermore reveals a publication in J. Endocr. (1988) 119, pages 159-165 which was concerned with characterization of pro-Opiomelanocortin (POMC)-related peptides in septic shock. The publication considers the question of increased endogenous opioid activity in septic shock and the influencing of selectivity by administration of steroids. A direct effect of an infectious process or the influencing of the measured values by antibiotics is not discussed. On the basis of the problem in said publication, there is no logical possibility of a generalized discussion of the reported results including other prohormone peptides. It is only in view of the teaching of the present invention, disclosed herein, that said publication can be interpreted retrospectively as a further indication of a general increase in prohormones in the case of sepsis.

Testing for further prohormones is to be regarded as a routine measure in view of the results disclosed herein and, if such tests lead to positive results and the determination of such further prohormones is used for the diagnosis of sepsis, use will therefore have been made of the teaching of the present Application.

TABLE 3

| | PCT [ng/ml] | Pro-ANF [pg/tube] | Pro-ADM [pg/tube | Pro-END [pg/tube | Pro-BNP [pg/tube |
|---|---|---|---|---|---|
| Normal Patients: | | | | | |
| A | 0.07 | 69.4 | 64 | 29.3 | 31.1 |
| B | 0.26 | 26.6 | 50.2 | 15.4 | 30.1 |
| C | 0.10 | 14.7 | 1.0 | 1.0 | 24.7 |
| D | 0.06 | 53.2 | 77.8 | 19.3 | 27.4 |
| E | 0.06 | 51.1 | 66.5 | 20.6 | 25.4 |
| F | 0.04 | 95.5 | 53.5 | 28.2 | 28.9 |
| G | 0.07 | 117 | 83.5 | 18.3 | 17.3 |
| H | 0.10 | 88.1 | 52.3 | 25.1 | 28.1 |
| I | 0.10 | 69.4 | 107 | 23.2 | 25 |
| J | 0.07 | 38.3 | 91.1 | 26.1 | 25.7 |
| K | 0.06 | 111 | 64.9 | 22.8 | 29.6 |
| L | 0.09 | 73.8 | 66.3 | 32.4 | 21.6 |
| M | 0.07 | 42 | 58.9 | 27.1 | 23.7 |
| N | 0.09 | 107 | 114 | 27.3 | 31.2 |
| O | 0.10 | 56.7 | 62.5 | 20.3 | 26.2 |
| P | 0.10 | 47.2 | 51.7 | 24.5 | 33.3 |
| Q | 0.12 | 155 | 72.5 | 34.6 | 36.7 |
| R | 0.13 | 92.1 | 64.7 | 29.6 | 35.2 |
| S | 0.12 | 153 | 100 | 34.7 | 36 |
| T | 0.11 | 78 | 69.6 | 27.1 | 37.7 |
| Sepsis Patients: | | | | | |
| 13a | 1.1 | 333 | 195 | 70 | 34.9 |
| 10a | 11.9 | 62.5 | 154 | 30.5 | 30.4 |
| 18b | 6.4 | 323 | 209 | 75.4 | 46.4 |
| 19b | 21.2 | 346 | 180 | 71.6 | 50.7 |
| 8a | 1.8 | 303 | 203 | 70.3 | 48.8 |
| 9a | 24.7 | 271 | 205 | 78.4 | 33.6 |
| 9b | 29.0 | 305 | 210 | 62.5 | 40.3 |
| 12b | 5.8 | 324 | 204 | 67.4 | 36.1 |
| 10b | 1.9 | 127 | 128 | 30.5 | 33.9 |
| 16a | 86.7 | 347 | 198 | 83.3 | 39 |
| 8b | 1.1 | 138 | 153 | 29.6 | 33.7 |
| 20a | 1.4 | 167 | 176 | 41.3 | 30.9 |
| 20b | 1.1 | 170 | 178 | 39 | 34.9 |
| 13b | 0.8 | 295 | 186 | 45.3 | 36.9 |
| 19a | 17.6 | 354 | 201 | 58.6 | 54.5 |
| 7b | 2.5 | 356 | 199 | 78.6 | |
| 7a | 2.9 | 345 | 197 | 148 | |
| 16b | 40.0 | 343 | 197 | 88.1 | 43.9 |
| 12a | 5.2 | 327 | 216 | 76.1 | 34.3 |
| 15b | 1.9 | 420 | 215 | 82.5 | 52 |

What is claimed is:

1. A method for the detection of sepsis in an individual suspected of having sepsis, comprising;
    contacting a blood, plasma or serum sample from the individual with an antibody which binds to a human peptide prohormone, other than procalcitonin, and/or a partial peptide of said prohormone, and
    determining the level of said human peptide prohormone and/or said partial peptide thereof, wherein an increase in said level compared to healthy individuals is indicative of sepsis,
wherein said partial peptide differs from the complete peptide sequence of said peptide prohormone by the absence of the first two amino acids at the amino terminus thereof or in the case of proendothelin consists of amino acids 18-50 of pre-pro-END.

2. The method of claim 1 for differential-diagnostic early detection of sepsis.

3. The method of claim 1 for assessment of the severity of sepsis or a sepsis-like systemic infection.

4. The method of claim 1 for assessment of the success of a therapeutic treatment of sepsis or a severe sepsis-like infection.

5. The method according to claim 1, wherein a partial peptide of a human prohormone is detected which differs from the complete peptide sequence of the human prohormone by the absence of the first two amino acids at the amino terminus thereof.

6. The method of claim 5 wherein said dipeptide is cleavable by dipeptidyl-aminopeptidase IV (DP IV; DAP IV or CD26).

7. The method of claim 1 wherein said antibody binds to an epitope in the peptide sequence of the prohormone which lacks its first two N-terminal amino acids.

8. The method of claim 1 further comprising determination of at least one other indicator of sepsis.

9. The method of claim 8 wherein said at least one other indicator is procalcitonin.

10. The method according to claim 1, wherein determination of the human prohormone and/or said partial peptide thereof is carried out as an immunoassay or a precipitation assay, and a diagnosis of the presence of sepsis or severe sepsis-like infections is made if the concentration of the human prohormone and/or said partial peptide determined is higher than the concentration observed in healthy persons.

11. The method of claim 1, wherein said prohormone is pro-END.

12. The method of claim 1, wherein said prohormone is pro-somatostatin.

13. The method of claim 1, wherein said prohormone is pro-GRP.

14. The method of claim 1, wherein said prohormone is pro-leptin.

15. The method of claim 1, wherein said prohormone is pro-neuropeptide Y.

16. The method of claim 1, wherein said prohormone is pro-neuropeptide YY.

17. The method of claim 1, wherein said prohormone is pro-opiomelanocortin.

18. A method for the detection of sepsis in an individual suspected of having sepsis, comprising;
    contacting a blood, plasma or serum sample from the individual with an antibody which binds to a human peptide prohormone other than procalcitonin and/or a partial peptide thereof, and
    determining the level of binding of said antibody, wherein an increase in said level compared to healthy individuals is indicative of sepsis,
wherein said partial peptide differs from the complete peptide sequence of said peptide prohormone by the absence of the first two amino acids at the amino terminus thereof or in the case of proendothelin consists of amino acids 18-50 of pre-pro-END.

19. The method of claim 18, wherein said prohormone is pro-END.

20. The method of claim 18, wherein said prohormone is pro-somatostatin.

21. The method of claim 18, wherein said prohormone is pro-GRP.

22. The method of claim 18, wherein said prohormone is pro-leptin.

23. The method of claim 18, wherein said prohormone is pro-neuropeptide Y.

24. The method of claim 18, wherein said prohormone is pro-neuropeptide YY.

25. The method of claim 18, wherein said prohormone is pro-opiomelanocortin.

* * * * *